United States Patent [19]

Standen et al.

[11] Patent Number: 5,777,172

[45] Date of Patent: Jul. 7, 1998

[54] PROCESS FOR THE PREPARATION OF BENZOPHENTHIONES AND BENZOPHENONES

[75] Inventors: Michael Charles Henry Standen, Clackmannan; Nicholas Charles Evens, Edinburgh, both of Scotland

[73] Assignee: Zeneca Limited, London, England

[21] Appl. No.: 737,863

[22] PCT Filed: May 16, 1995

[86] PCT No.: PCT/GB95/01101

§ 371 Date: Nov. 18, 1996

§ 102(e) Date: Nov. 18, 1996

[87] PCT Pub. No.: WO95/31435

PCT Pub. Date: Nov. 23, 1995

[30] Foreign Application Priority Data

May 16, 1994 [GB] United Kingdom ............. 9409735
Aug. 18, 1994 [GB] United Kingdom ............. 9416689

[51] Int. Cl.⁶ .................... C07C 45/42; C07C 325/02
[52] U.S. Cl. ............................. 568/332; 568/20
[58] Field of Search ......................... 568/20, 333, 332

[56] References Cited

FOREIGN PATENT DOCUMENTS 37730 11/1886 Germany.

OTHER PUBLICATIONS

Gattermann: "Uber gafarbte aromatische Thioketone", Berichte der Deutschen Chemischen Gesellschaft, vol. 28, 1895, pp. 2868-2877.
Bergreen: "Untersuchungen uber das Thiophosgen", Berichte der Deutschen Chemischen Gesellschaft, vol. 21, 1888, pp. 337-352, see p. 341.
Kitamura: Reaction between organic sulphur compounds and hydrogen peroxide. X. Thioketones, Chemical Abstracts, vol. 32, No. 5, Mar. 10, 1938, col. 1680, see abstract & Journal of Pharmaceutical Society of Japan, 1937, 57, 893-902.
Alper: "Desulphurisation and ortho–metallation reactions of dimanganese decacarbonyl", Journal of Organometallic Chemistry, vol. 73, No. 3, Jul. 9, 1974, pp. 359-364, see compounds II; p. 363, 1st paragraph.
Lynch et al: "The ketonimine dyestuffs and their derivatives", Journal of the American Chemical Society, vol. 55, No. 6, Jun. 1933, pp. 2515-2520, see p. 2518, last paragraph.
Klages et al: "Thioketyle 5. Isotrope ESR–Parameter von Thio–und Selenoketylen", Chemische Berichte, vol. 113, No. 6, Jun. 3, 1980, pp. 2255-2277, see compound 11.
Battaglia et al: "Kinetics and mechanism of 1,3–cycloadditions of benzonitrile N–oxides to thiobenzophenones", Journal of the Chemical Society, Section B: Physical Organic Chemistry, 1971, pp. 2096-2100, see compounds 2a–2f.
Lutteringhaus et al: "Uber den Bindungscharakter der Thiongruppe", Zeitschrift fur Chemie, vol. 10b, No. 7, 1955, pp. 365–367, see table 2.
Olah et al: "Synthesis of organic fluorine compounds XI. Preparation of several aromatic fluorine derivatives", Acta Chimica Academiae Scientiarum Hungaricae, vol. 7, 1955, pp. 85–92, See p. 87, 1st Paragraph; p. 89, Paragraph 12.
CA 113:77867 J. Chem Soc Chem Commun (1990) (8) 625–7, Tabuchi.
CA:120:269756–1994 Makioka Chem Lett (3) 611–14.
CA 108:130784 1987 Kamphuis J Chem Soc Perkin Trans 2(7) 907–11.
CA 105:24248, 1985 Baran Chem Lett (1985) (8) 1187–90.
CA Registry No. 53117–13–8 Oldest Reference 1974 CAReg.
Aldrich Chem Cat 1996 p. 528.

Primary Examiner—C. Warren Ivy
Assistant Examiner—Jean F. Vollano
Attorney, Agent, or Firm—Pillsbury Madison & Sutro LLP

[57] ABSTRACT

A process comprising the reaction of an optionally substituted benzene with thiophosgene in the presence of a Friedel Crafts catalyst for the preparation of the equivalent optionally substituted benzophenthione. The benzophenthiones are converted into the equivalent benzophenone derivatives by hydrolysis.

8 Claims, No Drawings

PROCESS FOR THE PREPARATION OF BENZOPHENTHIONES AND BENZOPHENONES

This application is the national phase of international application PCT/GB95/01101, filed May 16, 1995 which designated the U.S.

This invention relates to a process for the preparation of optionally substituted benzophenthiones, and especially 4,4'-difluorobenzophenthione and processes for their conversion to the corresponding benzophenones and to certain benzophenthiones.

4,4'-Difluorobenzophenone (4,4'-DFBP) is an important intermediate in the preparation of high performance polymers, such as PEEK and PES, but to make polymers with high performance properties it is essential to start with relatively pure 4,4'-DFBP, which is substantially free from the other positional isomers. Furthermore the 4,4'-DFBP, to be suitable for use in high performance polymers, must be substantially free from coloured impurities and polymeric by-products.

It is known to make di-substituted benzophenones by reaction of a mono-substituted benzene with phosgene in the presence of a Friedel-Craft's catalyst ("F-C Cat"), especially a Lewis acid, such as $FeCl_3$ or $AlCl_3$. While this reaction has a high overall yield, it leads to the production of a mixture of isomers in which the 4,4'-isomer, though predominant, represents only around 75% of the total mixture, the remainder being mainly 3,4'- and 2,4'-isomers.

It has now been surprisingly discovered that the use of thiophosgene ($CSCL_2$) in place of phosgene, in the acylation of fluorobenzene gives a mixture of isomeric difluorobenzophenthiones, containing a significantly higher proportion (>90%) of the 4,4'-isomer. This process is also applicable to other substituted, especially mono-substituted, benzenes. The thione(s) can be converted into the equivalent ketone(s) by hydrolysis or oxidation and the present invention also provides novel processes for effecting these conversions.

According to the present invention there is provided a process comprising the reaction of an optionally substituted benzene with thiophosgene in the presence of a Friedel-Craft's catalyst for the preparation of the equivalent optionally substituted benzophenthione.

In one aspect of the present invention, in which the benzene is mono-substituted, the process to form an optionally substituted benzophenthione may be represented by the following reaction scheme:

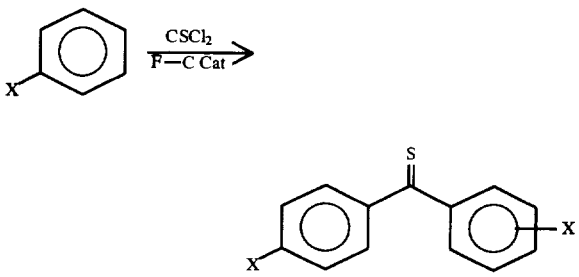

in which X is H, halogen, alkyl, alkoxy, CN and dialkylamino.

Where X is halogen it is preferably chlorine, fluorine or bromine and more preferably fluorine.

Where X is alkyl it is preferably $C_{1-6}$-alkyl, more preferably $C_{1-4}$-alkyl.

Where X is alkoxy it is preferably $C_{1-6}$-alkoxy, more preferably $C_{1-4}$-alkoxy.

Where X is dialkylamino it is preferably di($C_{1-6}$-alkyl) amino. X is preferably halogen, alkyl or alkoxy, more preferably —F, —Cl, $C_{1-4}$-alkyl or $C_{1-4}$-alkoxy.

It is further preferred that the benzene contains only one substituent (represented in the reaction scheme above by X) and that this is halogen, and more especially fluorine. The benzene may contain other substituents, provided they do not interfere with the reaction to produce the desired 4,4'-isomer. Examples of optionally substituted benzenes are benzene itself, fluorobenzene, chlorobenzene, brombenzene, toluene, anisole, cyanobenzene and diethylaminobenzene.

The Friedel-Craft's catalyst is preferably a Lewis acid, more preferably $FeCl_3$ or $AlCl_3$ and especially $AlCl_3$.

The reaction is preferably carried out at a temperature from 0° C. to 100° C., more preferably at from 0° C. to 80° C. and especially at from 0° C. to 40° C. Lower temperatures generally lower the reaction rate to below reasonable levels and higher temperatures tend to reduce the selectivity, reducing the proportion of 4,4'-isomer in the mixture. In the preferred temperature range the process typically takes approximately four hours to complete.

The reaction may be carried out in a medium which is liquid over the preferred temperature range, but it is preferred to use the optionally substituted benzene itself as the liquid medium, especially where the optionally substituted benzene is fluoro-benzene. Other suitable liquid media include aliphatic, cycloaliphatic and aromatic hydrocarbons and halogenated derivatives thereof, such as hexane, cyclohexane, dichloromethane and dichlorobenzene. However, with liquid media other than the optionally substituted benzene starting material, especially other aromatic solvents, there is a risk of acylation of the liquid medium to form by-products.

Disubstituted benzophenthiones, especially difluorobenzophenthiones, such as 4,4'-difluorobenzophenthimne, are believed to be novel compounds and such compounds form another feature of the present invention.

According to another aspect of the present invention there is provided a process for the preparation of an optionally substituted benzophenone comprising the reaction of the equivalently substituted benzophenthione with an acidic or basic aqueous solution.

Preferred acidic solutions comprise mineral or strong organic acids, such as HCl, $H_2SO_4$ and $CH_3COOH$ or mixtures thereof and preferred basic solutions comprise alkali and alkaline earth metal hydroxides, especially the former, such as NaOH, KOH and LiOH.

The hydrolysis is believed to be enhanced by the presence of a polar organic solvent and thus it is preferably performed in a mixture of water and a polar organic solvent.

Preferred polar solvents are lower alcohols and glycols, especially $C_{1-4}$-alkanols and $C_{2-4}$-glycols, such as methanol, ethanol, propanol, ethylene glycol and propylene glycol.

The hydrolysis is preferably carried out at a temperature from 40° C. to 110° C. and may be conveniently carried out at the boiling point of the aqueous/polar organic solvent mixture.

Preferred acidic solutions are aqueous HCl, especially in conjunction with methanol, aqueous HCl and $CH_3COOH$, and preferred basic solutions are aqueous NaOH, especially in conjunction with propanol.

Especially preferred acidic solutions are HCl in conjunction with methanol and a mixture of HCl and $CH_3COOH$.

According to a further aspect of the present invention there is provided a process for the preparation of an optionally substituted benzophenone comprising reacting a corresponding optionally substituted benzophenthione with an aqueous solution of an acid or a base followed by a polishing treatment.

This process has the advantage of producing a benzophenthione which is substantially free from polymeric byproducts and which is essentially colourless and thus is suitable for use as an intermediate in the preparation of high performance polymers. Suitable acids and bases are those described above.

The polishing treatment is preferably selected from an oxidation, a reduction, a carbon treatment, a silica treatment, or a distillation. Where the polishing treatment is an oxidation it is preferably achieved by reacting the optionally substituted benzophenone with an oxidising agent in a liquid medium. Suitable oxidising agents may be selected from peroxides such as hydrogen peroxide and sodium peroxide, oxides such as manganese dioxide, permanganates such as potassium permanganate, peracids such as perchloric acid, persulphates such as sodium persulphate, perchlorates such as sodium and potassium perchlorate, tungstates such as sodium tungstate, molybdates such as sodium and potassium molybdates, halogens such as chlorine, mixtures of cobalt acetate and sodium bromide, and air.

Suitable liquid media may be selected from acids such as acetic, hydrochloric and sulphuric acids.

A preferred oxidising agent is hydrogen peroxide. A preferred liquid medium is acetic acid.

Where the polishing treatment is a reduction it is preferably achieved by reacting the optionally substituted benzophenone with a reducing agent. A preferred reducing agent is a metal such as zinc in an acid such as acetic acid.

Where the polishing treatment is a carbon treatment this is preferably achieved by slurrying the benzophenone in a liquid medium with a finely divided carbon. A suitable liquid medium is a non polar organic liquid such as an alkane or cycloalkane. A preferred liquid medium is cyclohexane.

Where the polishing treatment is a silica treatment this is preferably achieved by slurrying the benzophenone in a liquid medium with finely divided silica. A suitable liquid medium is a non polar organic liquid such as an alkane or cycloalkane. A preferred liquid medium is cyclohexane. The above polishing treatments may be performed at a temperature from 0° C. to 100° C.

Where the polishing treatment is a distillation the distillation may be performed under atmospheric pressure or under vacuum.

The polishing treatment is preferably an oxidation more preferably an oxidation with hydrogen peroxide in acetic acid.

According to a further aspect of the present invention there is provided a process for the preparation of an optionally substituted benzophenone comprising reacting a corresponding optionally substituted benzophenthione with an oxidising agent.

This process has the advantage of producing a benzophenthione which is substantially free from polymeric byproducts and which is essentially colourless.

The reaction is preferably carried out in a liquid medium. The liquid medium may be an acid such as acetic or hydrochloric acid or the optionally substituted benzene from which the optionally substituted benzophenthione is prepared.

Suitable oxidising agents may be selected from those described above. A preferred oxidising agent is hydrogen peroxide.

The process may be carried out at a temperature from 30° C. to 120° C., preferably at a temperature from 50° C. to 100° C.

A preferred liquid medium is acetic acid and where the product is 4,4'-DFBP the preferred liquid medium is acetic acid or 4-fluorobenzene.

In a preferred embodiment of the present invention an excess of an optionally substituted benzene is reacted with thiophosgene in the presence of a Friedel-Craft's catalyst to give an optionally substituted benzophenthione which is oxidised in situ to the corresponding optionally substituted benzophenone by the addition of an oxidising agent.

The polishing treatment may be applied to the optionally substituted benzophenone irrespective of the way it was prepared.

The invention is illustrated by the following Examples in which all parts and percentages are by weight unless otherwise stated.

EXAMPLE 1

AlCl$_3$ (6 g, 0.045 moles) was added to fluorobenzene (78.6 g, ~0.8 moles) held at 0° C. in a stirred vessel fitted with a thermometer. Thiophosgene (5 g, 0.043 moles) was added slowly over about 30 minutes (exotherm) at such a rate as to keep the temperature of the reaction medium below 10° C. (~30 minutes) which caused the reaction medium to turn a bright red colour. The temperature was then allowed to warm spontaneously over about 4 hour during which HCl was evolved and finally the reaction mixture was heated to 40° C. over ~30 minutes until HCl evolution ceased.

The warm reaction mixture was drowned out into icewater (100 ml) to give a two phase system the organic layer being deep blue. This was extracted with a small amount of dichloromethane and the product, difluoro-benzophenthione isolated by evaporation of the solvent (yield, 9.2 g, 92% theory).

EXAMPLE 2

The product of Example 1 was hydrolysed to the corresponding benzophenone by refluxing for 3 hours with a solution of HCl and methanol in water and the product isolated by drown-out into water and filtration (6 g, MF 92°–98° C.). TLC analysis of a solution in 3:2 dichloromethane:benzene with a standard sample of 4,4'-difluorobenzophenone confirmed the authenticity of the product. HPLC analysis gave the following isomer ratios:

| | |
|---|---|
| 4,4'-isomer | 93.6% |
| 3,4'-isomer | 0.9% |
| 2,4'-isomer | 5.5% | which demonstrates the much greater regioselectivity of the present process when compared with the known process using phosgene.

A similar result is obtained when the HCl in methanol i replaced by NaOH in propanol.

EXAMPLE 3

A mixture of 4,4'-difluorobenzophenthione (51.g, 0.0. moles) and acetic acid (207.7 g) was heated to 75° C. an hydrogen peroxide (7.7 g of 67%, 0.15 moles) was adde portionwise. The temperature during the hydrogen peroxid addition was increased from 75° C. to 85° C.±5° C. Wate was added maintaining the reaction mixture at 70° C.±10° C The reaction mixture was allowed to cool. 4,4' difluorobenzophenone (96%) was precipitated and collecte by filtration.

EXAMPLE 4 i) A mixture of 4-fluorobenzene (480 g) and aluminiu chloride (142.4 g) was heated to 50° C.±2° C. and thiopho gene (118.6 g) was added over 90 minutes whilst maintaining the reaction temperature at 50° C.±2° C.

After a further 2 hours the reaction mixture was drowned out into water (800 cm³). A further 400 cm³ of water and 100 cm³ of 4-fluorobezene was added and the mixture separated.

The separated mixture of 4,4'-difluorobenzophenthione ("thione") and 4-fluorobenzene was distilled under vacuum to give the thione (199.6 g).

ii) The thione (199.6 g) was added to a mixture of acetic acid (800 cm³ of 99.7%) and hydrochloric acid (370 cm³ of 36%) before heating to 80° C. for 6 hours. The reaction mixture was distilled to leave 4,4'-difluorobenzophenone.

iii) The 4,4'-difluorobenzophenone was dissolved in acetic acid (100 cm³ of 99.7%) and heated to 80° C. hydrogen peroxide (329 g of 6%) was added over 2 hours and the reaction mixture held at 80° C. for a further 1 hour. water (470 cm³) was added and the reaction mixture was allowed to cool. The precipitated 4,4'-difluorobenzophenone was collected by filtration and washed acid free. The product was purified by recrystallisation from cyclohexane.

EXAMPLE 5 i) A mixture of 4-fluorobenzene (480 g) and aluminium chloride (142.4 g) was heated to 50° C.±2° C. and thiophosgene (118.6 g) was added over 90 minutes whilst maintaining the reaction temperature at 50° C.±2° C.

After a further 2 hours at 50° C.±2° C. the reaction mixture was analysed by gas chromatography to determine whether reaction was complete. After a further 30 minutes at 50° C.±2° C. the reaction mixture was added slowly to water (1000 cm³) maintaining the temperature at <50° C. After stirring for 30 minutes the mixture was separated and the aqueous layer was washed with fluorobenzene (2×75 g). The fluorobezene extracts were combined with the organic layer.

The separated mixture of 4,4'-difluorcbenzophenthione ("thione") and 4-fluorobenzene was distilled under vacuum to give the thione (230 g).

ii) Acetic acid (839 g of 99%) was added to the thione and heated to 80° C. Hydrochloric acid (420 g of 37%) was added in three portions each taking about 1 hour, the reaction mixture was held at 80° C. until gas chromotography indicated that the hydrolysis rate was slowing down. The reaction mixture was held at 80° C. for 1½ hours after all the hydrochloric acid was added.

The reaction mixture was cooled to ambient before acetic acid was recovered by distillation under vacuum to leave a crude difluorobenzophenone (220 g) as a melt.

iii) Acetic acid (1040 g of 99%) was added to the crude difluorobenzophenone from ii) above and the temperature was raised to 80° C. before adding hydrogen peroxide (200 g of 61%) in four portions. The reaction mixture was held at 80° C. for a further 1 hour before cooling and collecting the difluorobenzophenone (175 g) by filtration.

iv) A mixture of difluorobenzophenone from iii) above, cyclohexane (495 g) and carbon (8.75 g Norit CNl. Norit is a trade mark) was heated to 80° C., stirred for 30 minutes before screening through a heated filter to remove the carbon. The cyclohexane filtrates were heated to 80° C. before cooling to ambient and collecting the product by filtration, washing with propan-2-ol (3×50 g) and drying under vacuum at <40° C. to give difluorobenzophenone (117.7 g) which contained >99.98% of the 4,4'-isomer, <0.01% of the 2,4'-isomxer and <0.01% of the 3,4'-isomer.

EXAMPLE 6 i) The procedure of Example 5 i) was repeated.

ii) Acetic acid (531 g) was added to the thione (230 g) and heated to 65° C., whilst air was bubbled through the mixture. Hydrogen peroxide (75 g of 67%) was added in aliquots of approximately 10 g over about 7 hours whilst maintaining the temperature at 65° C.

After each aliquot was added the reaction mixture was sampled and the next hydrogen peroxide addition was started when the oxidation rate was slowing down. After the final hydrogen peroxide addition the reaction mixture was held for 1 hour at 65° C. The reaction liquors were allowed to cool to ambient temperature, the resultant crystallised difluorobenzophenone was collected by filtration and washed acid free with water, and dried under vacuum overnight at 40° C. to give difluorobenzophenone (162 g).

The acetic acid filtrates were diluted with water (150 g), heated to 65° C. then allowed to cool down to ambient to crystallise a 2nd crop of difluorobenzophenone (38.2 g).

The above procedure was repeated (dilution with 250 g of water) to obtain a 3rd crop of difluorobenzophenone (12.4 g).

iii) A mixture of difluorobenzophenone from ii) above, cyclohexane (566 g) and carbon (10.7 g Norit CNl) was heated to approximately 80° C.

The solution was stirred for ½ hour, then screened through a hot filter to remove the carbon. The cyclohexane filtrates were then reheated to approximately 80° C., (to ensure all BDF is dissolved) before cooling down to ambient. The crystallised difluorobenzophenone was filtered and washed with propan-2 -ol (3×50 g), before being dried under vacuum at <40° C. overnight to give difluorobenzophenone (128.7 g) which contained >99.8% 4,4'-isomer, 0.05% 2,4'-isomer and 0.09% 3,4'-isomer.

EXAMPLE 7

A mixture of anisole (26.1 g), heptane (50 cm³) and aluminium chloride (15 g) was held at 10° C. and thiophosgene (11.9 g) was added over 15 minutes maintaining the temperature at <15° C. The reaction mixture was heated to 70°–75° C. over 2 hours and held at this temperature for a further 2 hours. The reaction mixture was cooled to 20° C. and water (100 cm³) was added before extracting with dichloromethane (3×50 cm³). The dichloromethane extracts were combined and evaporated to give dimethoxybenzophenthione (39.4 g).

EXAMPLE 8

The product from Example 7 was hydrolysed in a mixture of acetic acid (84 cm³) and hydrochloric acid (42cm³) to give dimethoxybenzophenone.

EXAMPLE 9

The procedure of Example 7 was repeated except that toluene was used in place of the anisole and a reaction temperature of 50° C. was used to give dimethylrenzophenthione.

EXAMPLE 10

The procedure of Example 7 was repeated except that chlorobenzene was used in place of the anisole to give dichlorobenzophenthione.

EXAMPLE 11

The dichlorobenzophenthione of Example 10 was hydrolysed using the procedure of Example 8 to give dichlorobenzophenone.

We claim:

1. A process for the preparation of an optionally substituted benzophenone which comprises reacting the equivalently substituted benzophenthione with an aqueous solution of HCl in methanol.

2. A process for the preparation of an optionally substituted benzophenone which comprises reacting the equivalently substituted benzophenthione with an aqueous solution comprising a mixture of HCl and $CH_3COOH$.

3. A process according to claim 1 or 2 wherein the benzophenthione is a mixture of isomers of difluorobenzophenthione containing a greater than 90% isomeric excess of 4,4,'-difluorobenzophenthione.

4. A process for the preparation of a di-halosubstituted benzophenone which comprises reacting a benzene mono-substituted with a halogen, with thiophosgene in the presence of a Friedel-Craft's catalyst, and reacting the di-halosubstituted benzophenthione so produced with an aqueous solution of HCl in methanol.

5. A process according to claim 4 wherein the Friedel-Craft's catalyst is either iron trichloride or aluminum trichloride.

6. A process according to claim 4 or 5 wherein the benzene monosubstituted with a halogen is fluorobenzene.

7. A process according to claim 5 wherein the reaction between the benzene mono-substituted with a halogen and thiophosgene is carried out at a temperature of from 0° C. to 40° C.

8. A process according to claim 4 wherein the reaction between the benzene mono-substituted with a halogen and thiophosgene is carried out at a temperature of from 0° C. to 40° C.

* * * * *